US00PP27176P3

(12) United States Plant Patent
Bradford

(10) Patent No.: US PP27,176 P3
(45) Date of Patent: Sep. 20, 2016

(54) ***FUCHSIA* PLANT NAMED 'FWURB19-0'**

(50) Latin Name: ***Fuchsia* hybrid**
Varietal Denomination: FWURB19-0

(71) Applicant: Marie Bradford, Norwich (GB)

(72) Inventor: Marie Bradford, Norwich (GB)

(73) Assignee: Floranova Ltd (GB)

( * ) Notice: Subject to any disclaimer, the term of this patent is extended or adjusted under 35 U.S.C. 154(b) by 109 days.

(21) Appl. No.: 14/120,392

(22) Filed: May 16, 2014

(65) Prior Publication Data

US 2015/0334897 P1 Nov. 19, 2015

(51) Int. Cl.
*A01H 5/02* (2006.01)

(52) U.S. Cl.
USPC ..... Plt./300

(58) Field of Classification Search
USPC ..... Plt./300
See application file for complete search history.

*Primary Examiner* — Susan McCormick Ewoldt
(74) *Attorney, Agent, or Firm* — Cassandra Bright

(57) ABSTRACT

A new and distinct *Fuchsia* cultivar named 'FWURB19-0' is disclosed, characterized a strong branching habit, floriferous plants, exceptional cold tolerance and flowering response is not dependent upon day length. Flowers have a double layered corolla and are distinctively purple with a bright pink calyx. The new variety is a *Fuchsia*, typically produced as a garden or container plant.

1 Drawing Sheet

Latin name of the genus and species: *Fuchsia* hybrid.
Variety denomination: 'FWURB19-0'.

BACKGROUND OF THE INVENTION

The new cultivar is a product of a planned breeding program. The new variety originated from a cross pollination of the seed parent, an unnamed, unpatented proprietary selection of *Fuchsia* hybrid with the pollen parent a different unnamed, unpatented *Fuchsia* hybrid. The crossing was made during July of 2010, at a research greenhouse in Foxley, United Kingdom. 'FWURB19-0' was discovered by the inventor, Marie Bradford, a citizen of the United Kingdom, at the same research greenhouse during May 2011.

Asexual reproduction of the new cultivar 'FWURB19-0' was first performed in Foxley, United Kingdom at a research greenhouse by vegetative cuttings in September of 2011. 'FWURB19-0' has since produced several generations and has shown that the unique features of this cultivar are stable and reproduced true to type.

SUMMARY OF THE INVENTION

The cultivar 'FWURB19-0' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'FWURB19-0'. These characteristics in combination distinguish 'FWURB19-0' as a new and distinct *Fuchsia* cultivar:

1. Strong branching habit.
2. Floriferous plants.
3. Flowering response not dependent upon day length.
4. Double layer of petals in the corolla.
5. Hardy to −5° C., with foliage loss, but plants surviving.
6. Strong stems.
7. Flowers bright purple with a bright pink calyx.

PARENT COMPARISON

Plants of the new cultivar 'FWURB19-0' are similar to plants of the seed parent, in most horticultural characteristics, however, plants of the new cultivar 'FWURB19-0' differ in the following:

1. New variety has smaller flowers
2. Different flower color
3. Flowering response not dependent upon day length, whereas the seed parent flowers under long day conditions.
4. Better branching from a pinch.

Plants of the new cultivar 'FWURB19-0' are similar to plants of the pollen parent in most horticultural characteristics, however, plants of the new cultivar 'FWURB19-0' differ in the following:

1. New variety flowers later.
2. New variety has much stronger stems.
3. New variety has a double layered corolla.
4. New variety is a much more vigorous plant.

COMMERCIAL COMPARISON

Of the many *Fuchsia* varieties known to the inventor, the most similar is *Fuchsia* 'Marcia' U.S. Plant Pat. No. 13,760. The new variety differs from plants of 'Marcia' in the following:

1. New variety flowers later.
2. New variety has much stronger stems.
3. New variety has a double layered corolla.
4. New variety is a much more vigorous plant.
5. new variety has better cold tolerance.

BRIEF DESCRIPTION OF THE PHOTOGRAPH

The accompanying photograph in FIG. 1 illustrates in full color a typical plant of 'FWURB19-0' grown outdoors in Santa Paula, Calif. This plant is approximately 30 weeks old, shown in a 10 inch pot. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Colour Chart, 2007, except where general terms of ordinary dictionary significance are used. The following observations and measurements describe 'FWURB19-0' plants in a commercial greenhouse in Santa Paula, Calif. Temperatures ranged from 10° C. to 29° C. night and day. No artificial light, photoperiodic treatments or chemical treatments were given to the plants. Natural light conditions were approximately 2500 to 4000 fc of light. Measurements and numerical values represent averages of typical plant types.

Botanical classification: *Fuchsia* hybrid 'FWURB19-0'.

PROPAGATION

Propagation method: Vegetative Cuttings.
Time to initiate roots: About 2 weeks at 15° C. to 22° C.
Root description: Fine, densely fibrous.

PLANT

Age of plant described: Approximately 17 weeks from 3 rooted cuttings.
Pot size of plant described: 8 inch.
Height: Approximately 17 cm from soil line of pot to top of foliar and uppermost flowering plane.
Plant spread: Approximately 54 cm.
Growth rate: Rapid.
Growth habit: Semi-upright center, edge of plant pendulous.
Branching characteristics: Free branching.
Length of primary lateral branches: Average 22 cm.
Diameter of lateral branches: Approximately 0.3 cm.
Quantity of primary lateral branches: Approximately 18.
Characteristics of primary lateral branches:
- *Color*.—Near RHS Greyed-Red 181C.
- *Texture*.—Glabrous.
- *Strength*.—Strong, flexible.

Internode length: Average range 1.8 to 4.5 cm

FOLIAGE

Leaf :
- *Arrangement*.—Opposite.
- *Quantity*.—Approximately 6 to 12 fully expanded leaves per primary lateral branch.
- *Average length:* 6.1 cm, including petiole.
- *Average width*.—2.7 cm.
- *Shape of blade*.—Ovate.
- *Apex*.—Acute
- *Base*.—Oblique.
- *Margin*.—Denate.
- *Texture of top surface*.—Glabrous.
- *Texture of bottom surface*.—Glabrous.
- *Aspect*.—Mostly flat.
- *Color*.—Young foliage upper side: Near RHS Green 137A. Young foliage under side: Near RHS Green 138A. Mature foliage upper side: Near RHS Green 137A. Mature foliage under side: Near RHS Green 137C.
- *Venation*.—Type: Pinnate. Venation color upper side: Near RHS Yellow-Green 144C. Venation color under side: Near RHS Green 143D.
- *Attachment*.—Stalked.
- *Petiole*.—Length: Average 1.1 cm. Diameter: Average 0.15 cm. Texture: Glabrous. Color: Upper surface: Near RHS Greyed-Red 181B. Lower surface: Near RHS Yellow-Green 144B.

FLOWER

Natural flowering season: Year round under temperate conditions. Flowering is not dependent upon day length.
Inflorescence and flower type and habit: At least 2 flowers emerge singly from each axil. Flowers emerge at different times, resulting in flowers of different maturity at each axil. Flowers are symmetrical and composed of a corolla surrounded by a decorative fused calyx. Flowers face outwardly.
Flowers per plant: Approximately 40 fully open flower and 20 buds on a mature plant.
Flower longevity on plant: Approximately 1 week for individual flowers.
Persistent or self-cleaning: Self-cleaning.
Flower size (petals and sepals only, not including protruding stamen and style):
- *Length*.—Approximately 3.1 cm.
- *Width*.—Approximately 3.9 cm.

Bud:
- *Shape*.—Oblong, with an inflated sphere at terminal end.
- *Length*.—2.5 cm.
- *Diameter*.—1.8 cm.
- *Color*.—Near RHS Red 56C, heavily flushed Red-Purple 58B.

Corolla:
Petals (measured from separation at top of tube):
- *Number*.—Average 8 to 12.
- *Length*.—Approximately 3.1 cm.
- *Width*.—Approximately 2.1 cm.
- *Shape*.—Obovate.
- *Aspect*.—Strong inward curl.
- *Margin*.—Entire.
- *Texture*.—Glabrous, all surfaces.
- *Appearance*.—Matte.
- *Apex*.—Obtuse.

Color:
- *When opening*.—Upper surface: Near RHS Violet N89C, base near Red-Purple N66D. Lower surface: Near RHS Violet N88B, base near Red-Purple N66D.
- *Fully opened*.—Upper surface: Near RHS Purple N78A, base streaked near Purple 75C. Lower surface: Near Purple N78B, base streaked near Purple 75C.
- *Fading*.—Upper surface: Near RHS Purple N78C, base streaked near Purple 75D. Lower surface: Near RHS Purple N78C, base streaked near Purple 75D.

Calyx:
- *Form*.—Funnelform base, separating approximately 25% from base, to flare out into 4 large decorative deltoid shaped sepals. Sepals reflexed and curled back.
- *Fused section*.—Length: Approximately 1.6 cm. Diameter: Approximately 0.9 cm.
- *Unfused section*.—Length: Approximately 2.8 cm. Diameter: Approximately 1.9 cm.
- *Sepal texture*.—Glabrous all surfaces.

*Appearance*.—Shiny.
*Apex*.—Acute.
*Color*.—Upper Surface: Near RHS Red-Purple N57B. Lower Surface: Near RHS Red-Purple N57B.
*Fragrance*.—None.

REPRODUCTIVE ORGANS

Stamens:
*Number* (*per flower*).—Typically 8.
*Filament length*.—Average 4.5 cm.
*Filament color*.—Near RHS Red-Purple N57B.
*Anthers*.—Shape: Globular. Length: Approximately 0.1 cm. Color: Near RHS Red 56C.
*Pollen*.—Amount: Moderate, colored near Red 56D.
Pistils:
*Quantity per flower*.—1.
*Length*.—Approximately 5.1 cm.
*Style*.—Length: Approximately 4.6 cm. Color: Near Red-Purple N57A.
*Stigma*.—Shape: Globular. Color: Near Red-Purple N57A. Ovary: Length: Approximately .5 cm. Diameter: Approximately .4 cm. Color: Near RHS Green 143B.

OTHER CHARACTERISTICS

Seeds and fruits: Not observed to date.
Disease/pest resistance: Neither resistance nor susceptibility to normal diseases and pests of *Fuchsia* has been observed.
Temperature tolerance: Tolerates temperatures from approximately −5° C. to 38° C.
Drought tolerance: No tolerance for drought.

What is claimed is:

1. A new and distinct cultivar of *Fuchsia* plant named 'FWURB19-0' as herein illustrated and described.

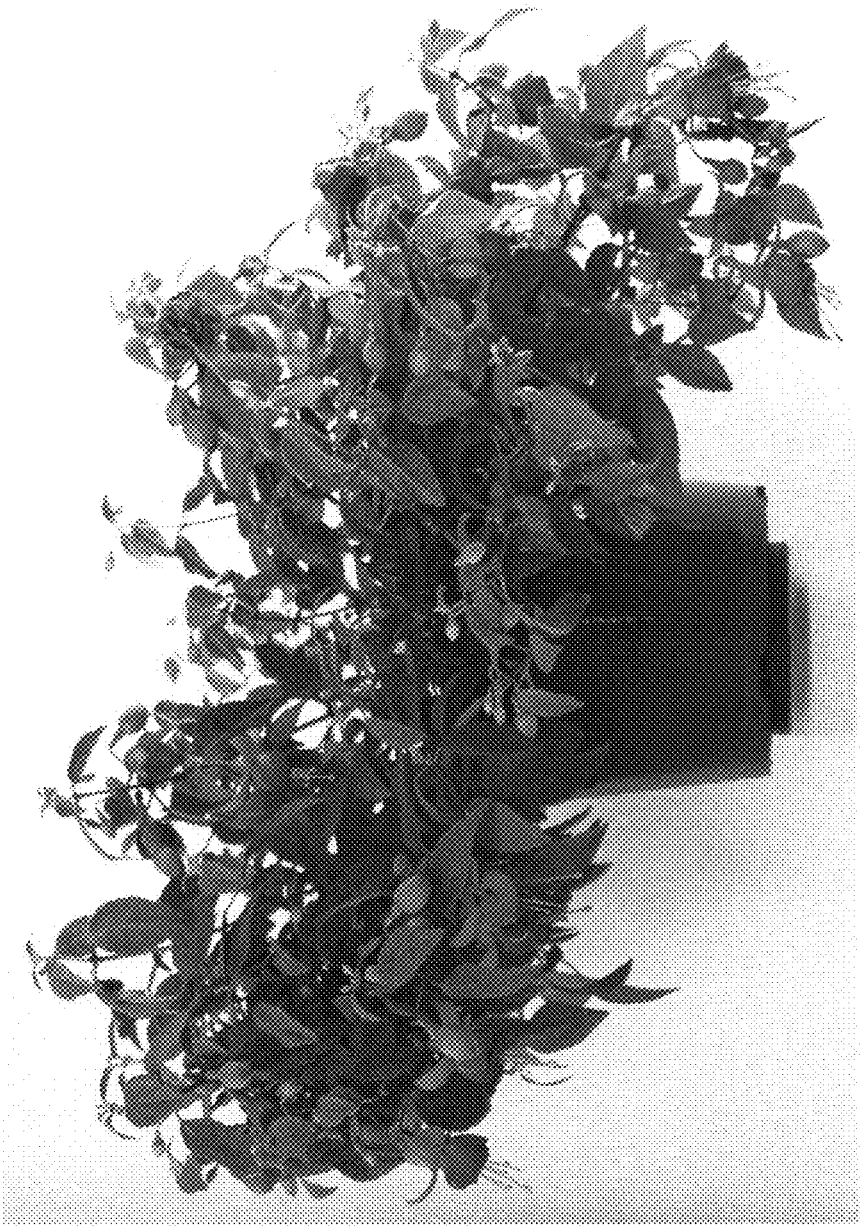

* * * * *